United States Patent [19]

Pieniak

[11] 4,413,623
[45] Nov. 8, 1983

[54] LAMINATED STRUCTURES HAVING GATHERED AND UNGATHERED MARGINAL PORTIONS AND METHOD OF MANUFACTURING THE SAME

[75] Inventor: Heinz A. Pieniak, Chicago, Ill.

[73] Assignee: Johnson & Johnson Baby Products Company, New Brunswick, N.J.

[21] Appl. No.: 235,187

[22] Filed: Feb. 17, 1981

[51] Int. Cl.³ .............................................. A61F 13/16
[52] U.S. Cl. .................................. 604/365; 156/160; 156/229; 156/269; 156/297; 428/78; 428/198; 428/230; 428/231
[58] Field of Search ................ 428/198, 230, 231, 78; 128/284; 156/160, 229, 269, 297

[56] References Cited

U.S. PATENT DOCUMENTS 2,197,188  4/1940  Lilley .................................. 428/231

Primary Examiner—Marion McCamish
Attorney, Agent, or Firm—Martha A. Michaels

[57] ABSTRACT

A laminated structure, such as a disposable diaper is provided which includes elastic in the margin to provide gasketing about the legs and, if desired, an improved fit about the waist. A method is provided for placing elastic only in the areas to be gathered and removing the unused elastic. In the method stretched elastic is intermittently adhered to a web substrate along a longitudinal line at the terminating portion of the gasketed area. The elastic is then severed adjacent the adhered portions and the unused elastic is removed.

15 Claims, 9 Drawing Figures

LAMINATED STRUCTURES HAVING GATHERED AND UNGATHERED MARGINAL PORTIONS AND METHOD OF MANUFACTURING THE SAME

BACKGROUND OF THE INVENTION

Recent years have seen an increased demand for inexpensive apparel and the development of new and inexpensive components of construction and method of construction of articles of apparel. In certain instances, there is a demand for apparel that is very inexpensive and, indeed, disposable. New elastomeric materials and methods of incorporating them into portions of the garment have been developed to meet the desire to fit these types of garments to a human form. For example, U.S. Pat. No. 3,639,917 discloses the use of a strip of a heat recoverable elastomeric material to gather the cuff of a disposable hospital gown.

Disposable diapers have been marketed which include an elastic or stretch member in the longitudinal side edges of the disposable diaper to provide elasticity about the leg of the infant when the diaper is applied. Examples of such stretchable fitted diapers which have elastic members disposed in the longitudinal side edges of the diaper are shown in U.S. Pat. Nos. 3,860,003 and 4,050,462. Elastic contraction of the longitudinal sides of the diaper which are the leg and thigh encircling portion of the diaper once placed on an infant compresses the diaper about the leg of the infant. This compression reduces leakage at the leg and upon tightening, leakage is reduced even further. However, if the fit is too tight, irritation can result on this tender portion of the thigh, especially when the diaper is wet. There are also a number of patents which disclose means for making the waist-encircling portion of a disposable diaper elastic for tighter fit of the diaper about the waist of the wearer, for example, as shown and described in U.S. Pat. Nos. 3,995,637 and 3,995,640.

Disposable diapers usually comprise a facing and a backing layer which are substantially co-extensive and a somewhat smaller absorbent core or panel interposed between the facing and backing layers. The facing and backing layers are adhered together about their perimeter by hot melt adhesive or other adhesive material as is well known. In producing stretch or elastic diapers, an elastic member in its stretched or partially stretched state is interposed between the facing and backing sheets along one or more edges of the diaper. The elastic member is adhered either to the facing and/or the backing sheets by adhesive or similar means and allowed to relax to produce elastic sections at the edges of the diaper. An example of a method for inserting elastic members in disposable diapers is disclosed in U.S. Pat. No. 4,081,301.

The incorporation of these elastic members into disposable diapers has increased both the cost of materials used in the diaper and the cost of construction of disposable diapers. With solid elastic members, it is necessary to adhere the edges of the facing and backing sheets together either directly or by their mutual attachment to the elastic member.

When adhesively securing such an elastic member into a disposable diaper, the adhesive chosen must be elastomeric or must be applied in a discontinuous pattern or the glue may make the diaper too stiff to gather.

In commonly assigned co-pending patent application, Ser. No. 210,507 filed Nov. 26, 1980, there is disclosed apertured elastic members which have substantial advantages over other types of elastic members in that they are simpler and more economical to insert and function very well by providing a good fit with a minimum of irritation.

In order to provide the elasticity in the central portion of the side edge of the diaper, it previously had been necessary to insert elastic which, if extended in its stretchable state, would extend the entire length of the side of the diaper. Elasticity is required only in the central portion of the side edges of the diaper, i.e., that portion which encircles the wearer's leg. Thus, in each of the prior art diaper structures, elastic which is either unused or has been rendered non-elastic, resides in the ungathered portion of the side margin and thus elastic material is wasted.

The present invention is an improvement on laminated structures, disposable diapers and a method for inserting the elastic such that there is no waste of elastic material.

SUMMARY OF THE INVENTION

The present invention provides an improved, laminated structure having a marginal area with a first portion of the marginal area being gathered and a second portion not being gathered which provides improved fit about a portion of a human body and a method of making the same. The laminated structure comprises first and second layers of flexible, gatherable material and an elastic disposed between the substrates in the marginal area thereof only in the portion of the margin to be gathered. The elastic member is any suitable elastic, but preferably is of a thermoplastic substance described hereinafter. Most preferably, the elastic member comprises a plurality of longitudinally extending elastic elements. The longitudinal elements are transversely connected over a portion of their length and define apertures therebetween. The first and second layers are secured together through at least some of the apertures thus producing the laminated structure.

The laminated structure of the present invention may be used in any fitted garment, but perhaps is most suited for use in inexpensive and disposable apparel. The laminated structure can be incorporated into the sleeve cuff, the leg encircling portion, about the neck and the waist of an article of apparel. In particular, the laminated structure may be incorporated into both the waist and thigh encircling portions of a disposable diaper or other disposable undergarment. The improved laminated structure of the present invention reduces the pressure applied to the skin of the wearer and in a disposable diaper or a disposable undergarment, reduces the possibility of irritation and rash when wet.

In accordance with the present invention, the improved elastic member can be readily inserted in a stretched condition between the first and second layers only in the portion to be gathered and these layers easily adhere together to hold the elastic member in place, at high speeds, with good reliability and at reduced costs. The portion of elastic, which is not adhered or retained in the garment, is removed and can be recycled for subsequent use. Thus, the laminated structure contains elastic only in the portions where it is desirable to gather the first and second layers.

The elastic member has a width of from about one-fourth inch to about two inches and the member may have a thickness of from 1 to 50 mils and preferably from about 5 to 20 mils. The elastic member may be made of any standard film materials which are stretchable and are recoverable and have a modulus of elasticity at 100% elongation of from about 20 to about 2,000 lbs. per sq. inch. In a disposable diaper, in accordance with the present invention, the elastic member may be disposed between the backing and the facing sheet of the diaper in the longitudinal side margins of the diaper and/or disposed between the backing and facing sheet of the diaper in the waist portions either in the front or back or both.

In one method of the manufacture of a laminated structure of the present invention, a web substrate is provided having a first portion to be gathered and a second portion to remain ungathered. An elastic member is fed in a stretched condition immediately adjacent to one side of the web structure. The elastic member is adhered intermittently to the web substrate along at least one longitudinal line adjacent what will be the terminating portions of the elastic member. The elastic member is then severed at the terminating portions of the section which is to remain ungathered and removed. Thus, elastic is provided only in the area that is to be gathered and no elastic is present in the portion which is to remain ungathered. The elastic structure so produced can then be incorporated into a laminated structure whereupon two layers are laminated with the elastic in between.

A particular advantage of the present invention is that elastic, which can be expensive, is not wasted. Furthermore, the method of manufacture can be applied to many types of elastic. A thermoplastic reticulated elastic recently developed has been found to be particularly desirable in a disposable diaper to provide gasketing around the legs. However, until discovery of the present invention there had not been a satisfactory method for providing a product having elastic present only in the areas to be gathered. Particularly, there had not been a satisfactory method known for inserting reticulated elastic in a laminated structure only where gathered areas are desired. When using reticulated elastic members in accordance with the present invention, the insertion of the member into the product and the adherence thereto is greatly simplified and there is no wasted elastic. The elastic which is not used is removed and can be recycled for further use or can be returned to a melt and new elastic made therefrom. The apertured portion insures a uniform intermittent lamination between the elastic and non-elastic layers and combined with non-interconnected portions which reduces the criticality of adhesive application. Also the apertures combined with adhesion through the apertures provides that the final lamination acts or performs in its stretch recovery and similar elastic properties with great uniformity and a very gentle gathering of the laminate layers. This allows for greater certainty in predicting the quality and functionality of the final product.

DESCRIPTION OF THE PREFERRED EMBODIMENTS

For a laminated structure of the present invention, the elastic member is a readily stretchable, preferably thermoplastic member, that possesses a certain minimum elastic recovery.

The term "elastic" as used herein, refers to sheets, films, ribbons, filaments, and the like which have a recovery of at least 90% when elongated to within 10% of their field point and measured in accordance with the following formula:

$$\% \text{ Retraction} = \frac{Le - Lt}{Le - Lo} \times 100$$

where;

Lo = original length of sample
Le = fully extended length
Lt = length of sample measured 3 seconds after release from extended length The thickness of the elastic member may be from about 1 to 5 mils and is preferably from about 5 to 20 mils. It has a width of from ¼ inch to about 2 inches and, preferably in diaper applications, widths of from about ½ inch to 1 inch have been found satisfactory. For ease of stretchability the modulus of elasticity of the elastic member at 100% elongation should not exceed about 2,000 lbs. per sq. inch. The modulus of elasticity is preferably substantially less than 2,000 lbs. per sq. inch and most preferably is about 75 to about 400 lbs. per sq. inch.

Figure 1:
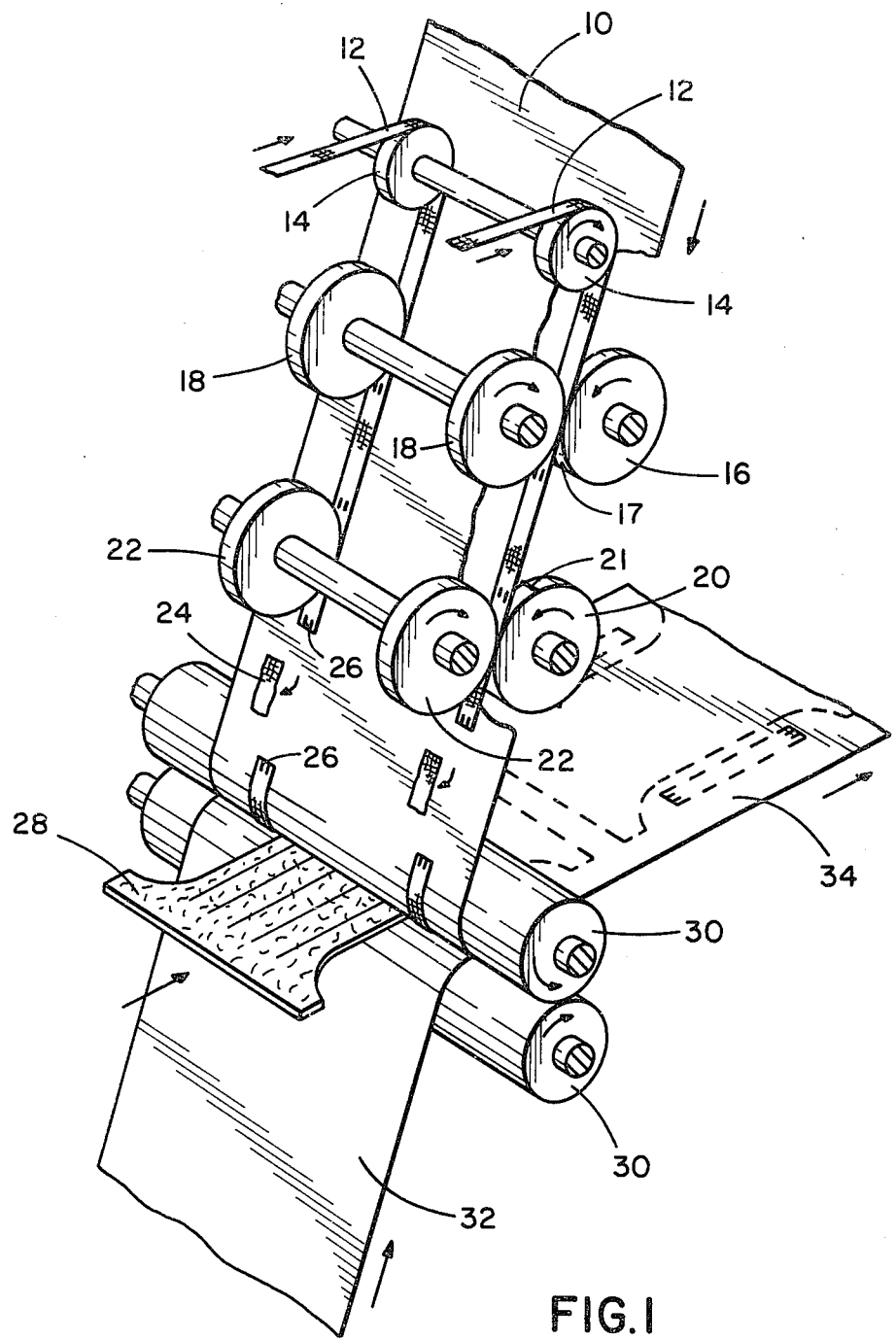
FIG. 1 is a perspective view substantially illustrating operation of the method of the present invention.

Referring now to FIG. 1, a perspective view of a schematic illustration of one way of making the products of the present invention is shown. A web substrate 10 such as a polyester diaper facing is provided. Stretched reticulated elastic, or a satisfactory elastic member 12 is fed in such a manner as to be placed immediately adjacent the web substrate in the desired location. Both the reticulated elastic and the web substrate are fed through rolls 16 and 18. These roll are provided with heated projections 17 which, when pressing against the polyester, provide sufficient heat and pressure to render the reticulated elastic thermoplastic along at least one longitudinal strand so as to adhere the longitudinal strand to the web substrate only along the longitudinal strands so treated. If the elastic is not reticulated, the same kind of longitudinal lamination is carried out. The spot laminated elastic and web substrate then move forward to another set of rolls, 20 and 22. The roll 20 has a transverse projection 21, which is heated. The heated projection 21 is placed against the laminate immediately past the laminated longitudinal portion. In this way the heat ruptures the elastic transversely severing it in the desired location.

Figure 1A:
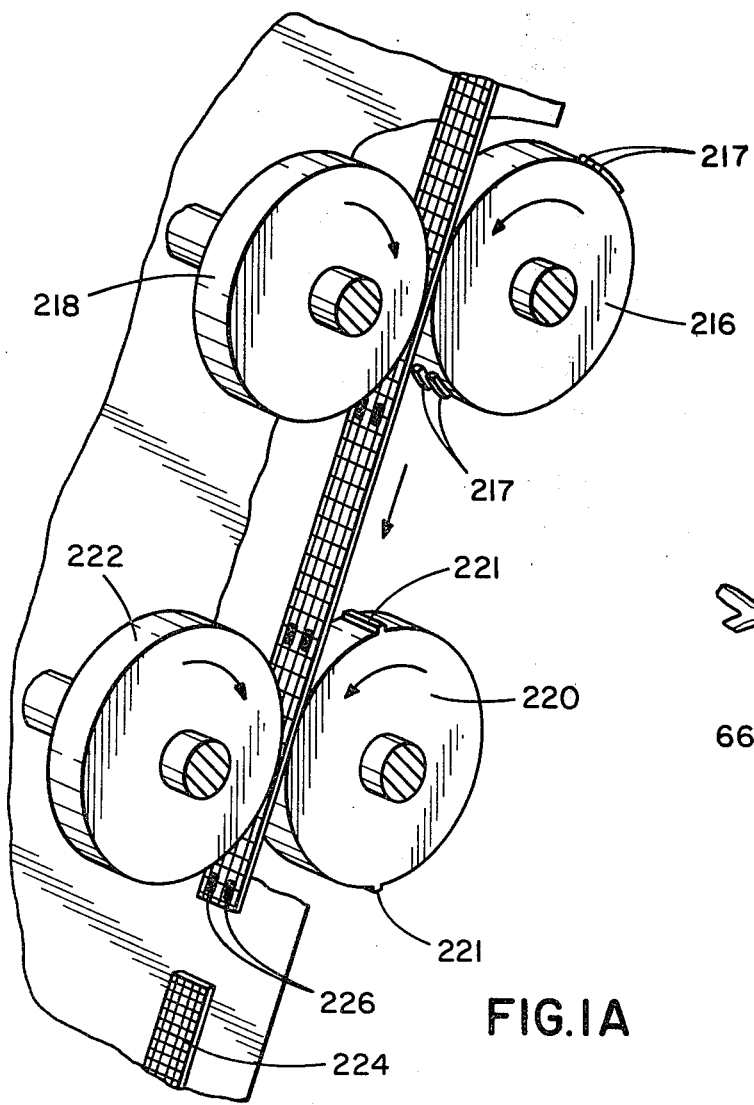
FIG. 1A is an enlarged perspective view of a section of FIG. 1 identified as between lines A—A and B—B.

In the enlarged view shown in FIG. 1A it can be seen more easily how the longitudinal strands of reticulated elastic are adhered 226 to the web substrate. A roll 218 acts in concert with another roll 216 to feed both the substrate web and the reticulated elastic 212 between the rolls and have sufficient heat and pressure 217 for the spot lamination to take place. Continuing down the line in FIG. 1A, it is seen that the elastic 212 is fed through rolls 220 and 222 whereupon the reticulated elastic 212 is severed by use of the heated projections 221. The reticulated elastic portion 224 not adhered to the web substrate is removed. Removal of the unadhered reticulated elastic may take place by use of vacuum, a wire brush, a pick, or any other desirable means.

Referring again to FIG. 1, after the reticulated elastic 24 is removed, it can be seen that the reticulated elastic is adhered to web substrate 10 in stretched pieces or strips. These strips are placed so as to lie in the central portion of a diaper panel 28 so that upon continuation of movement of the web substrate 10 another web substrate 32, in this case the backing for a diaper, is placed on the other side of panel 28 and the two web substrates are laminated along each margin 34 by use of laminating rolls 30 to produce a series of diapers with reticulated elastic in stretched condition placed only in the central portion of the diaper in each margin.

Figure 2:
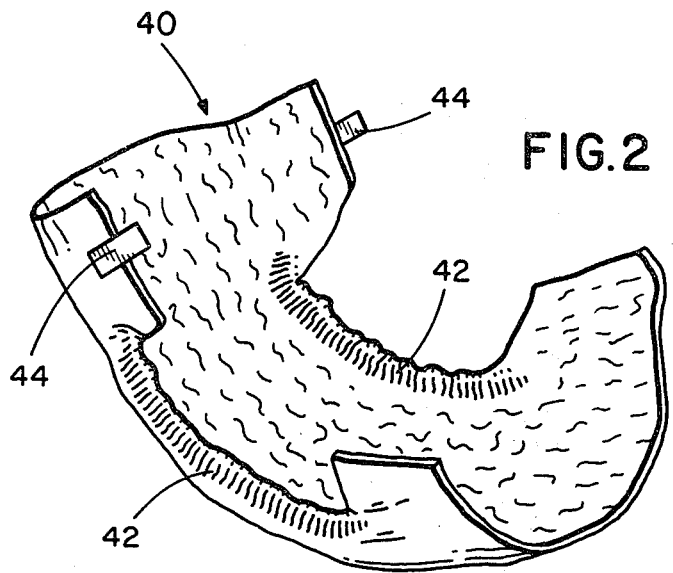
FIG. 2 is a perspective view illustrating a disposable diaper in accordance with the present invention.

FIG. 2 is a perspective view illustrating a disposable diaper 40 of the present invention. The diaper 40 has gathered portions at 42 but does not have elastic in the remainder of the diaper margin areas. The diaper when worn is secured about the wearer by use of the tape tabs 44.

Figure 3:
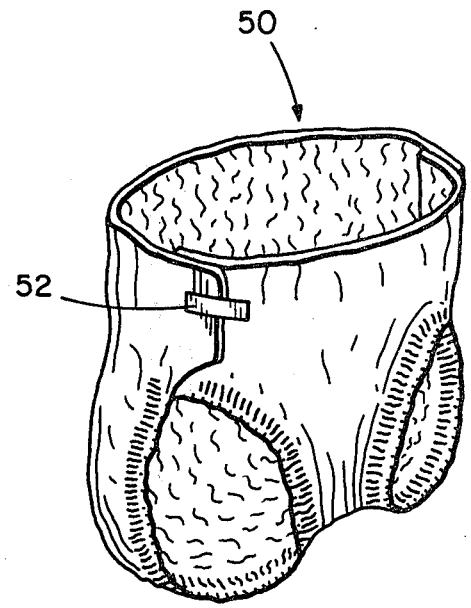
FIG. 3 is a perspective view of the disposable diaper of FIG. 2 viewed in the configuration it assumes when disposed about a wearer.

FIG. 3 is a perspective view of a disposable diaper 50 which is the same diaper as in FIG. 2 but viewed in the configuration it assumes when disposed about a wearer. It is secured about the wearer with tape tabs 52.

Figure 4:
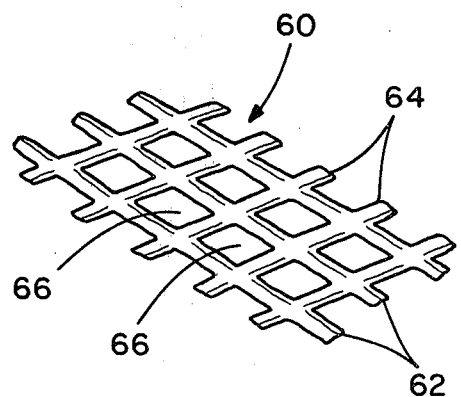
FIG. 4 is an enlarged perspective view illustrating a reticulated elastic member which may be used in the method and products of the present invention.

FIG. 4 is an enlarged perspective view showing a portion of a reticulated elastic member 60. The reticulated elastic member 60 consists of longitudinal strands 62 and transverse strands 64. The longitudinal strands and transverse strands are adhered at the junctions and thus provide apertures 66. During the practice of the present invention one or more longitudinal strands 62 are adhered in selected areas to a web substrate by means of heat or adhesive or any other means to adhere the elastic longitudinally in the selected areas. Subsequent to adhering the elastic longitudinally 62 to the web substrate in the desired areas, heat or other severing means may be used to sever the elastic transversely in an area adjacent the adhered area, thus leaving at least a portion of the elastic adhered to the web substrate.

Figures 5, 6:
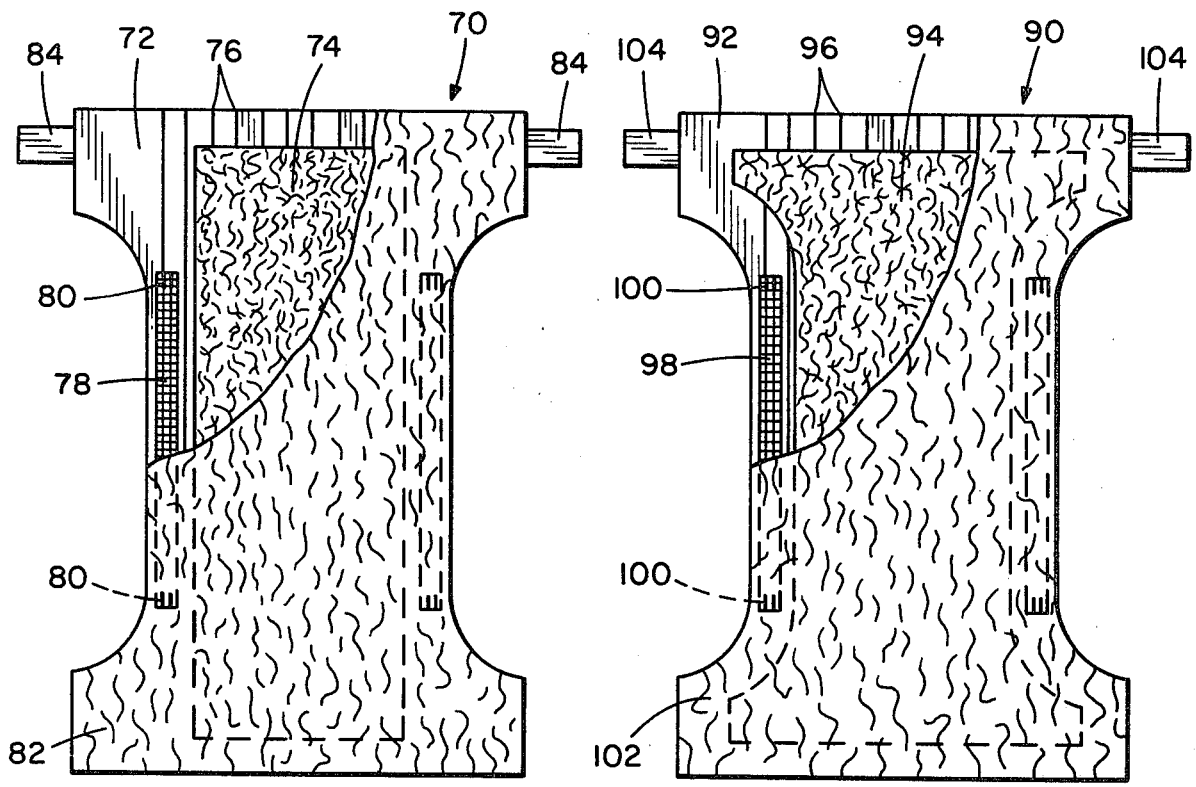
FIG. 5 is a plan view of one embodiment of the disposable diaper of this invention with a portion broken away to show interior detail.
FIG. 6 is a plan view of another embodiment of the disposable diaper of this invention with the portion broken away to show interior detail.

Referring now to FIG. 5, a plan view of a diaper 70 is illustrated. The diaper 70 consists of a backing sheet 72, an absorbent pad 72, and a moisture-permeable facing 82. In the side margin in the central portion, reticulated elastic 78 is laminated in a stretched condition. At the terminal ends 80, at least one longitudinal strand is laminated to the facing 82 prior to formation of the final laminated product. The absorbent panel 74 is held in place by glue lines 76. When the diaper is to be worn, it is secured about the wearer by tape tabs 84.

Referring now to FIG. 6, a further embodiment of the present invention is illustrated. A diaper 90 has substantially the same structure as that of FIG. 5 except that the absorbent panel 94 is narrower in the central portion. The backing sheet 92 is adhered to the absorbent panel 94 by use of glue lines 96. The reticulated elastic 98 is laminated in the margins in the central portion and is previously adhered to the facing 102 at the terminal portions 100. The diaper is affixed about the wearer by use of tape tabs 104.

Figures 7, 8:
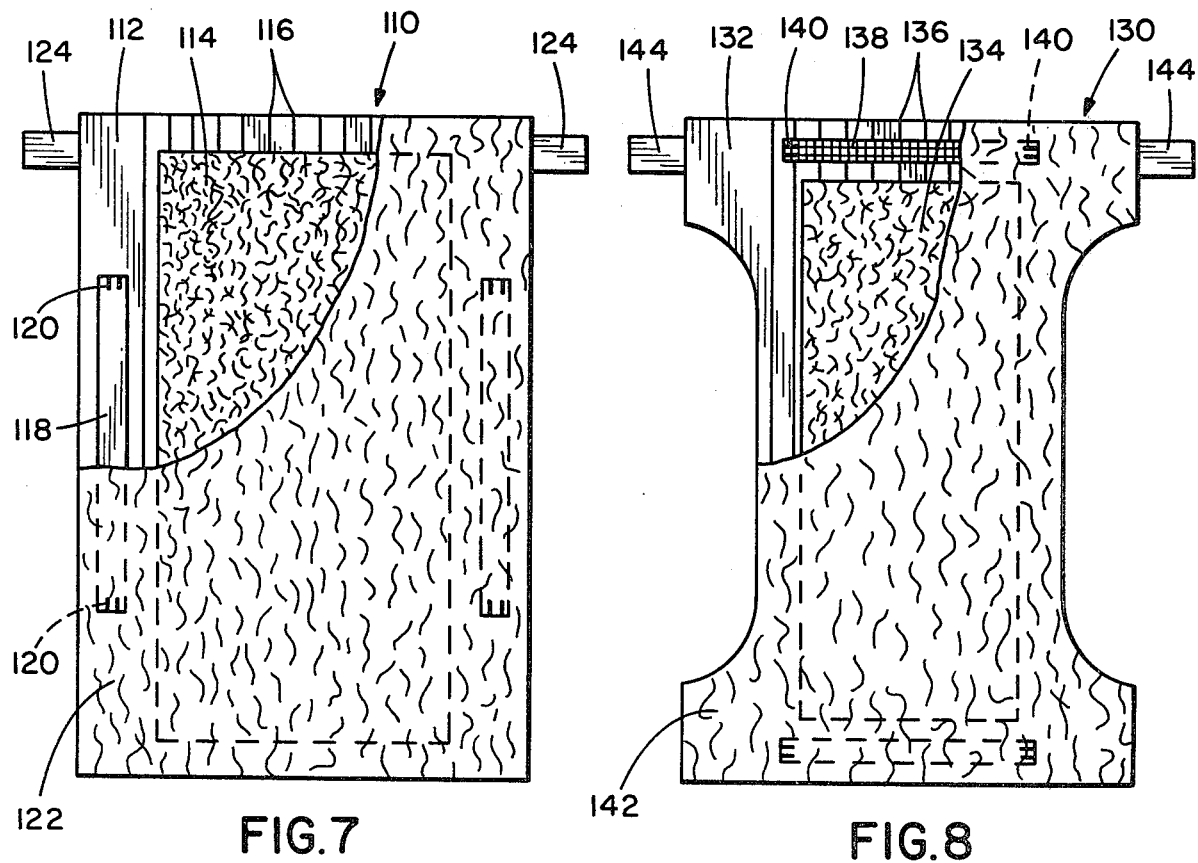
FIG. 7 is a plan view of a further embodiment of the disposable diaper of this invention with a portion broken away to show interior detail.
FIG. 8 is a plan view of a still further embodiment of the disposable diaper of this invention with a portion broken away to show interior detail.

FIG. 7 illustrates a rectangular diaper 110 which is constructed of a moisture-impermeable backing 112, a panel of fibrous material 114 held in place by glue lines 116. Elastic 118 is placed in each side margin and adhered to the facing longitudinally at the terminal ends 120. The elastic is a thermoplastic elastic film. The facing 122 is laminated in the margins to the backing 112 in a conventional manner. The diaper is secured in position on the wearer by use of tape tabs 124.

FIG. 8 illustrates a shaped diaper 130 wherein reticulated elastic 138 is placed in each of the margins at the waist band ends of the diaper. An absorbent panel 134 is superimposed on a moisture-impermeable backing 132. A moisture-permeable facing 142 is superimposed on the side opposite the backing with respect to the absorbent panel 134. The panel 134 is held in place by glue lines 136. The reticulated elastic 138 is adhered at its terminal portions 140 on at least one of the longitudinal strands. The gathering in the waist portion affords a secure fit about the waist of the wearer. The diaper is secured in position at the waist about the wearer by tape tabs 144.

The elastic members suitable for use in the diapers contemplated may be made from films extruded, calendered, or otherwise formed to the desired thickness and pattern of openings utilizing low stretch modulus materials made from any rubbery elastic material. Specifically, unvulcanized thermoplastic compositions which are made of an elastomeric component and an optional compatible modifier which is a thermoplastic polymer of a relatively low molecular weight but solid at ambient temperatures have been found to make suitable elastic members for use in accordance with the present invention.

Illustrative of the elastomeric components suitable for present purposes are block copolymers which comprise terminal thermoplastic polymer blocks and at least some non-terminal or intermediate elastomeric polymer blocks. Block copolymers of this general type may be prepared using a step-wise polymerization initiator, e.g., an organolithium compound. Such block polymerization techniques are well known in the art.

The elastic component can be linear or radial $A^1$—$B$—$A^2$ block copolymers or mixtures thereof with simple $A^1$—$B$ block copolymers wherein $A^1$ and $A^2$ can be alike or different and represent a thermoplastic polymer block, such as poly(vinyl arene) block, and B represents an elastomeric polymer block such as a conjugated diene or a lower (i.e., $C_1$-$C_4$) alkene. The modifier component is a low molecular weight thermoplastic polymer having an average molecular weight of about 500 to 7,500 and is present in the composition in an amount of about zero to about 200 parts by weight per 100 parts by weight of the elastomeric component.

A preferred thermoplastic film composition for the elastic members comprises an elastomeric component which contains, as a major constituent thereof, an unvulcanized linear block copolymer of the general configuration,

wherein $A^1$, $A^2$ and B have the same meaning as hereinabove. In these block copolymers, the A-blocks are derived from styrene or styrene homologues, and the B-blocks are derived from conjugated dienes or lower alkenes. The thermoplastic polymer modifier is compatible with the elastomeric component and associates principally with the thermoplastic terminal blocks of the aforesaid unvulcanized block copolymer. The thermoplastic polymer modifier preferably has an average molecular weight of about 1000 to about 3000, and is present in the film composition in an amount of about 80 to 200 parts by weight per 100 parts by weight of the elastomeric component.

The preferred $A^1$—B—$A^2$ block copolymers have A-blocks derived, i.e. polymerized or copolymerized, from styrene or styrene homologues; and B-blocks derived from conjugated dienes, such as isoprene or butadiene, or from lower alkenes such as ethylene and butylene. Small proportions of other monomers also may enter into the block copolymers themselves. The individual A-blocks can have an average molecular weight of at least about 6000, preferably in the range of about 8000-30,000, and the A-blocks constitute about 5-50 percent, preferably about 10-30 percent, by weight of the block copolymer. The average molecular weight of the B-blocks for linear $A^1$—B—$A^2$ block copolymers preferably is in the range of about 45,000-180,000 and that of the linear copolymer, itself, preferably is in the range of about 75,000-200,000. The average molecular weight of the radial $A^1$—B—$A^2$ block copolymers preferably is in the range of about 125,000-400,000. The term "linear block copolymer" (or copolymers) includes branched $A^1$—B—$A^2$ copolymers as well as unbranched $A^1$—B—$A^2$ copolymers.

The radial $A^1$—B—$A^2$ copolymers useful for manufacture of elastic members for diapers of this invention are of the type described in U.S. Pat. No. 3,281,383 to Zelinski. et al and conform to the following general formula: (A—$B_n$X), wherein A is a thermoplastic block polymerized from styrene or styrene homologues, B is an elastomeric block derived from conjugated dienes or lower alkenes, as indicated above, X is an organic or inorganic connecting molecule with a functionality of about two to four as described in U.S. Pat. No. 3,281,383, or possibly with a higher functionality as described in the Article entitled "New Rubber is Backed by Stars" appearing on Page 35 of the June 11, 1975 issue of Chemical Week. As used hereinabove, "n" has a value corresponding to the functionality of X.

The preferred elastic member is highly thermoplastic and, though elastomeric, is unlike rubber in that it exhibits a relatively sharp melting point and is capable of being heat shaped. Also, the elastic member can form permanent heat seals to substrates such as non-woven fabrics or the like, at relatively low heat sealing temperatures, generally not above about 350° F. The member is very flexible, extensive and soft, and normally exhibits a Gurley stiffness of about one or less at a film thickness of one mil.

Elastic members especially suitable for use in disposable diapers may be made from combinations of thermoplastic rubber and amorphous polypropylene. The thermoplastic rubbers used in such combinations are block copolymers having blocks of polybutadiene or polyisoprene, and blocks of polystyrene. A review article discussing these materials is "Structure and Properties of Block Polymers and Multiphase Polymer Systems: An Overview of Present Status and Future Potential," by S. L. Aggarwal. *Polymer*, Vol. 17, November 1976, Pages 938-956. Two representative types of thermoplastic rubbers useful in these combinations are the linear block copolymers (A—B—A) having a midblock of polybutadiene or polyisoprene and end-blocks of polystryene, and the "star" or "radial" block copolymers having from 4 to 20 "arms" connected to a common center. Each arm is an A—B block copolymer, the inner portion being polybutadiene or polyisoprene, with the outer portion being polystyrene.

The material added or combined with the thermoplastic rubber, primarily to improve processability, while still retaining the characteristic rubbery properties of the rubber, is amorphous polypropylene. Amorphous polypropylene is a known material. It is essentially atactic polypropylene having an isotactic content of not more than about 20 weight percent, and preferably not more than about 10 weight percent.

The amorphous polypropylene is employed in an amount sufficient to improve the processability of the thermoplastic rubber when extruding thin films or sheets. The exact minimum amount of amorphous polypropylene which must be employed varies somewhat from case to case, but it is usually of the order of about 10 weight percent, based on weight or rubber plus amorphous polypropylene, although the proportion may be as low as about 5 weight percent (on the same basis) in some cases. The upper limit of polypropylene will also vary from case to case, depending on the nature of the ingredients and the use intended for the product. At proportions above about 35 weight percent (on the same basis), a significant reduction in the characteristic rubbery elastomeric properties of the product begins to occur. This may be acceptable for some uses, and not for others. Thus, the upper limit of amorphous polypropylene would be that point at which the product still retains significant rubbery elastomeric characteristics.

Other conventional materials, employed in the usual amounts, can be employed in the mixture for their known purposes. Such materials include pigments, anti-blocking agents, stabilizers, anti-oxidants, ultraviolet stabilizers, bonding aid, and the like.

Especially suitable reticulated elastic materials which may be used in accordance with the present invention are those described in the co-pending patent application of William G. F. Kelly, Ser. No. 179,593 filed Aug. 19, 1980. A specific reticulated elastic member which we have found suitable for producing the disposable diapers of the present invention is that described in Example 2 of the aforementioned patent application wherein the reticulated elastic member has the following composition:

|  | Parts by Weight |
| --- | --- |
| Solprene 418 | 66.9 |
| Solprene 414 | 20.0 |
| Elvax 460 or UE 630 | 8.0 |
| Kenamide E | 0.8 |
| Ionol (anti-oxidant) | 0.2 |
| Irganox 1010 (anti-oxidant) | 0.2 |

"Solprene P414" is a 60/40 butadiene/styrene radial block copolymer, and "Solprene P418" is an 85/15 isoprene/styrene radial block copolymer. These materials are further characterized as follows:

|  | Solprene P414 | Solprene P418 |
| --- | --- | --- |
| Molecular weight | 150,000 | 300,000 |
| Specific gravity | 0.95 | 0.92 |
| Melt flow, 5 kg @ 200° C. | 2.2 | 2.2 |
| Inherent viscosity | 0.80 | 1.16 |
| Solution visosity, cps. |  |  |
| 20% wt. in toluene | 230 | 900 |
| 25% wt. in toluene | — | 2300 |

"Elvax" 460 is an ethylene/vinyl acetate copolymer having a Melt Index (by ASTM D 1238) of 2.2–2.8 and a vinyl acetate content of 17.5 to 18.5 weight percent.

"Petrothene" UE 630 is an ethylene/vinyl acetate copolymer having 17 weight percent vinyl acetate and a Melt Index of 0.5.

"Kenamide E" is a fatty acid amide.

In some embodiments of the disposable diaper of the present invention, the elastic member is a member which may be made elastic by imparting heat or other forms of energy to the member to shrink the member and provide it with elastic characteristics. A portion of the member is so treated to provide the elastic means while other portions are not treated.

The heat-shrinkable films which may be used as elastic members in the disposable diapers of the present invention may be the polyolefin films which have been oriented to a degree and which will then become elastic when heat shrunk. Usually, a preferred technique for orienting the polyethylene film to provide the heat shrunk elastic properties is by irradiation such as suggested in British Pat. No. 866,820. Also, useful as the heat shrunk elastic members are the copolymers of ethylene and vinyl acetate, ethylene and ethyl acrylate, and the like. The forming of such copolymers is well known and specific methods of forming such materials are disclosed in U.S. Pat. Nos. 2,200,429 and 2,953,551. After the copolymer is formed and made into a film, it is given the proper orientation as described in the previously mentioned British Pat. No. 866,820.

The apertured elastic member useful in accordance with the present invention may also be made from other materials; such as, natural rubber, the synthetic rubbers, and the like. The member may be made in the form of a film with intermittent longitudinal portions that are reticulated separated by non-reticulated portions. The film is slit into the desired width and inserted between the backing and facing sheet of the diaper.

Broadly, the elastic members may be made from materials having elongations of from 20 to 1000 percent and preferably from about 50 to 500 percent with recoveries in the range of 20 to 100 percent and preferably from 70 to 100 percent. The material should have a force to stretch it 100 percent of from 30 to 2000 grams.

The important factor to remember is that when the material is placed in the end product, the material be elastic, as previously defined, so it functions as such an elastic in the final product. For example, in the diaper leg band area, the member should have 90 percent or better recovery in very short periods of time and preferably, almost simultaneously, the member should also require a relatively low amount of force to stretch the leg band area back to its original or non-gathered length. Such force should be less than 200 grams and may be as low as 20 grams.

Several different types of facing materials may be used for the disposable products of the present invention. For example, the facing may be a non-woven web made of a mixture of fibers consisting predominantly of inexpensive short cellulosic fibers such as short wood pulp fibers or cotton linters in amounts of 75% to 98%, the balance being textile length fibers such as rayon as described in U.S. Pat. No. 3,663,348 to Liloia et al.

Non-woven facing material suitable for use in the disposable products of this invention can have fabric weights in the range from about 0.5 to 5 oz. per sq. yard and densities of less than 0.15 grams/cc, generally in the range of 0.05 to about 0.1 grams/cc. The dry strength of the facing sheet for a fabric having a weight of about 1.5 oz. per sq. yard is at least 0.15 lbs. per inch of width in the machine direction and at least 0.1 lb. per inch of width in the cross direction. Such fabrics have good elongation, loft, softness and drape characteristics. Facings may also be made of an apertured non-woven fabric which is formed, for example, in accordance with the teachings of commonly assigned U.S. Pat. Nos. 2,862,251, 3,081,514 and 3,081,515. Furthermore, facings may also be made from other types of fabrics such as those disclosed and described in U.S. Pat. No. 3,485,706 to Evans. Such facings can be made of naturally occurring fibers, synthetic fibers, or blends thereof. Typical facing sheets made of polyester-type fibers may have a weight of about 0.75 oz. per sq. yard.

The facing may be the same size as and coterminus with the backing or alternatively, the facing may be wider than the facing and have its edges inwardly folded so that the facing is coterminus with the backing as is shown in FIG. 3 of U.S. Pat. No. 3,612,055. In the latter case the elastic members may be secured above the inwardly folded side edges of the facing. In addition, facings may be made from non-apertured materials such as non-woven isotropic webs or apertured polyolefin or polyester films having the desired moisture permeability. In all of the aforementioned facings, the material should be relatively hydrophobic so as to retard wicking within the facing.

The moisture absorbent batt or panel of a desired shape but smaller than the facing and backing can be formed in accordance with the teachings of U.S. Pat. No. 3,612,055 to Mesek et al.

A suitable backing material for the disposable undergarments embodying the present invention can be an opaque polyolefin, for example, polyethylene about 0.001 inch thick. Another suitable material for this purpose is polyethylene-teraphthalate, having a thickness of about 0.005 inches. In use the disposable diaper of the present invention is applied to the baby by laying out the diaper on a single flat surface and placing the baby thereon. The waist underlying end of the diaper is that end having the fastener means and the other end of the diaper extends downwardly between the baby's legs. Next, the downwardly extending diaper is brought up between the baby's legs to a position covering the perineum and contiguous with the front portion of the baby's waist. The diaper thereafter is secured to the baby by placing the corners of the waist portion of the abdomen-covering end as far around the baby's waist as they will go and by bringing the corners of the underlying end of the diaper into an overlapping relationship with the aforementioned corners so that the diaper snuggly encircles the baby's waist and provides a custom fit. The adhesive tape fasteners are then prepared for use and the diapers brought in a desired position by simply urging the pressure-sensitive adhesive surface of the tape tab in contact with the adjacent outer surfaces of the opposite corner of the diaper.

In some instances, particularly when the wearer is an adult, it may be desirable to have a second fastener available that can be applied just above the thigh of the wearer and below the standard fastener to improve and secure the fit of the stretch diaper.

The method of manufacturing the elastic structure of the present invention comprises feeding the reticulated elastic member in a stretched condition to a position adjacent a web substrate. At least one longitudinal strand is adhered to the web substrate by use of heat or adhesive or other means at the terminating portions of the length desired for the reticulated elastic member. The elastic member is then severed beyond the adhered portions and the elastic which is severed and not adhered is removed. The structure is then laminated to another web with an absorbent panel inserted between the two web substrates. The lamination of the web substrates to each other holds the reticulated elastic in position in a stretched state by adhering the two web substrates one to the other through the apertures of the reticulated elastic. Upon completion of lamination and release of any tension, gathers appear in the elastic region where the elastic has been laminated. The individual elastic laminated structures are then conveyed away and packaged in a known manner.

The foregoing description of the drawings are illustrative and are not to be taken as limiting. Still other variations and modifications are possible without departing from the spirit and scope of the present invention.

What is claimed is:

1. A method for making an elastic structure which can be separated into a series of individual elastic structures comprising:
   (a) feeding a web substrate having in the feed direction alternate first portions to be gathered and second portions to remain ungathered;
   (b) feeding an elastic member in a stretched condition immediately adjacent to one side of said web substrate;
   (c) adhering said elastic member intermittently to said substrate along at least one longitudinal line at the terminating portions of each first portion to be gathered;
   (d) severing said elastic member at points adjacent to the adhered portions thereof so as to remove the unadhered portion of the elastic member adjacent to each second portion of the web substrate; and
   (e) removing the unadhered elastic member portion from the individual elastic structures.

2. The method of claim 1 wherein the elastic member is a thermoplastic elastic member.

3. The method of claim 2 wherein the elastic member is adhered by use of heat and pressure.

4. The method of claim 1 wherein the elastic member is adhered by use of an adhesive substance.

5. The method of claim 1 including the additional step of laminating a second web substrate to the web substrate on the side opposite the elastic member.

6. A method for making an elastic structure which can be separated into a series of individual elastic structures comprising:
   (a) feeding a web substrate having alternate first portions to be gathered and second portions to remain ungathered;
   (b) feeding an elastic member in a stretched condition immediately adjacent to one side of said web substrate, said elastic member comprising a plurality of longitudinally extending elements transversely connected with elastic elements to define apertures therebetween;
   (c) adhering at least one longitudinally extending element to the web substrate at least at the terminating portions of each first portion to be gathered;
   (d) severing said elastic member at points adjacent to the adhered portions thereof so as to remove the unadhered portion of the elastic member adjacent to each second portion of the web substrate; and
   (e) removing the unadhered elastic member portion from the individual elastic structures.

7. The method of claim 6 wherein the elastic member is a thermoplastic reticulated elastic member.

8. The method of claim 7 wherein the longitudinally extending elastic elements which are adhered are adhered by use of heat and pressure.

9. The method of claim 6 wherein the longitudinally extending elements which are adhered are adhered by use of an adhesive substance.

10. The method of claim 6 including the additional step of laminating a second web substrate to the web substrate on the side opposite the elastic member.

11. A method of attaching a pair of elastic members intermediate the opposing waist band portions of absorbent pads contained in a continuously moving web of interconnected disposable diapers to form a pair of discrete elastic leg bands in each of said diapers cut from said web, said method comprising the steps of:
   (a) providing a first web substrate having alternate first portions to be gathered and second portions to remain ungathered;
   (b) feeding a pair of stretched elastic members perpendicular to said first and second alternate portions adjacent to one side of said first substrate, each member comprising a plurality of longitudinally extending elastic elements transversely connected with classtic elements to define apertures therebetween;
   (c) adhering at least one longitudinally extending element of each stretched elastic member to the first web substrate at least at the terminating portions of each first portion to be gathered to provide a stretched adhered elastic portion in each first portion to be gathered;
   (d) severing said elastic members at points adjacent to the adhered portions away from the adhered portion to be gathered;
   (e) removing the unadhered severed elastic member portion;
   (f) feeding a second web substrate adjacent to the adhered stretched elastic member on the side opposite the first web substrate;
   (g) adhering the first and second web substrate together along substantially the entire length and through the portions of the elastic members defining apertures; and
   (h) cutting said web transversely into discrete disposable diapers to provide discrete disposable diapers having a gathered portion and an ungathered portion.

12. The method of claim 11 wherein the longitudinally extending elements which are adhered are adhered by use of heat and pressure.

13. The method of claim 11 wherein the longitudinally extending elements which are adhered by use of an adhesive substance.

14. A laminated structure having a marginal area with a first portion of said marginal area being gathered and a second portion of said marginal area not being gathered to provide improved fit about a portion of the human body comprising:
- (a) first and second layers positioned adjacent one another, said layers being formed of flexible, gatherable material; and
- (b) an elastic member disposed between said layers in the marginal area thereof, said elastic member comprising a plurality of longitudinally extending elastic elements transversely connected with elastic elements to define apertures therebetween, a portion of at least one of said longitudinally extending elastic elements being heat sealed to one of said first and second layers in said marginal area being gathered, said first and second layers being secured together through at least some of said apertures to provide a gathered marginal portion, said second portion of said marginal area not being gathered having any remaining portion of said elastic member severed and removed thereby being free of any said elastic member.

15. A disposable diaper comprising:
- (a) a moisture-permeable facing layer;
- (b) an absorbent panel at one side of said facing layer, said absorbent panel being smaller than said facing layer so that marginal portions of the facing layer extend outwardly beyond the edges of said absorbent panel;
- (c) a moisture-impervious backing layer at the side of said absorbent panel opposite said facing layer, said backing layer being larger than said absorbent panel and substantially coterminous with said facing layer so that marginal portions of the backing layer extend outwardly beyond the edges of said absorbent panel;
- (d) means bonding said facing and backing layers to one another; and
- (e) an elastic member adhered in the central portion of each side margin, the unadhered ends of said elastic members being severed and removed from said side margins, said adhered elastic member comprising a plurality of longitudinally extending elastic elements transversely connected with elastic elements and said adhered elastic member having at least one longitudinally extending elastic member being sealed to one of said facing and said backing layers at least at each end of said adhered elastic element.

* * * * *